United States Patent [19]

Nishida et al.

[11] 4,168,303

[45] Sep. 18, 1979

[54] LYOPHILIZED NATIVE GAMMA GLOBULIN PREPARATION FOR INTRAVENOUS ADMINISTRATION

[75] Inventors: Masayuki Nishida, Osaka; Sadao Yabushita, Daito; Shigeru Fujita, Minoo; Toshiyuki Saki, Kyoto, all of Japan

[73] Assignee: The Green Cross Corporation, Osaka, Japan

[21] Appl. No.: 913,493

[22] Filed: Jun. 7, 1978

[30] Foreign Application Priority Data

Jul. 19, 1977 [JP] Japan .................................. 52-87128

[51] Int. Cl.² ............................................ A61K 37/06
[52] U.S. Cl. ................................. 424/85; 260/112 B; 424/86; 424/87
[58] Field of Search ............................ 424/85, 86, 87; 260/112 B

[56] References Cited

U.S. PATENT DOCUMENTS

| | | | |
|---|---|---|---|
| 2,793,203 | 5/1957 | Schultze et al. | 424/86 |
| 3,466,368 | 9/1969 | Sela et al. | 424/85 |
| 3,903,262 | 9/1975 | Pappenhagen et al. | 424/86 |
| 3,966,906 | 6/1976 | Schultze et al. | 424/85 |
| 4,021,540 | 5/1977 | Pollack et al. | 424/86 |
| 4,027,010 | 5/1977 | Kiselev et al. | 424/87 |
| 4,087,519 | 5/1978 | Trepo | 424/86 |

FOREIGN PATENT DOCUMENTS

2606118  8/1976  Fed. Rep. of Germany ............. 424/85

*Primary Examiner*—Donald G. Daus
*Assistant Examiner*—M. C. Eakin
*Attorney, Agent, or Firm*—Cushman, Darby & Cushman

[57] ABSTRACT

Freeze-drying of an aqueous solution of human native gamma globulin having an anticomplementary activity of 20 ($C'H50$) or less in the presence of 0.06 to 0.26 part by weight of a neutral inorganic salt for 1 part by weight of the gamma globulin gives an immunoactive lyophilized native gamma globulin preparation which has undergone neither increase in anticomplementary activity nor deterioration in antibody activity during the freeze-drying and is safe for use in intravenous administration.

8 Claims, No Drawings

LYOPHILIZED NATIVE GAMMA GLOBULIN PREPARATION FOR INTRAVENOUS ADMINISTRATION

This invention relates to a gamma globulin preparation which manifests no side effects when administered intravenously and to a method of its production. More particularly, it relates to a lyophilized gamma globulin preparation suitable for intravenous administration by freeze-drying an aqueous solution of human gamma globulin in the presence of a neutral salt to supress the increase in anticomplementary activity as well as to a method of its production.

Preparations, particularly of gamma globulin containing IgG as major constituent, among immunoglobulins of the plasma protein, have been useful extensively for prophylaxis and therapy of various microbisms. Intravenous administration of this preparation, however, causes serious anaphylactoid side effects accompanying sudden decrease in blood pressure. For this reason, administration of the gamma globulin preparation has heretofore been exclusively through intramuscular route. Intramuscular administration, in general, has disadvantages in that (1) the recipient suffers from pain at the side of injection, (2) dosage is limited, (3) about half a dose is lost at the side of injection due to proteolysis, and (4) transfer of the drug from the site of injection to the blood stream requires 1 to 2 days.

To overcome the above disadvantages, development of an intravenously administrable gamma globulin preparation has heretofore been attempted and a number of preparative methods have been proposed. In order to render the gamma globulin preparation intravenously administrable, it is necessary to suppress the above-noted anaphylactoid reaction. The occurrence of such reactions has been interpreted on the basis of liberation of biologically active factors such as anaphylatoxoid substances and vascular wall-permeable factors caused by the activation of complement in the blood as the result of combination with macro-molecular aggregates which are formed by polymerization of immunoglobulins and present in most of the immunoglobulin fractions collected by human plasma fractionation.

Consequently, studies have been conducted to decline the complement-fixing ability (anticomplementary activity) of the aggregated macromolecules, thus rendering the gamma globulin preparation intravenously administrable. As the result, there have become available so-called chemically modified gamma globulin preparations for intravenous administration prepared by treating gamma globulin with an acid or $\beta$-propiolactone or by splitting the gamma globulin molecule into fragments such as Fab, F (ab')$_2$, and Fc by digestion by enzymes such as pepsine and plasmin. However, in the case of acid treatment, it is said that on administration the gamma globulin molecules tend to reaggregate, thereby increasing the anticomplementary activity, while digestion by an enzyme brings about excessive fragmentation of gamma globulin molecules, resulting in not only reduced biological half-life, but also decline of most important antibody titer and antibody spectrum of the gamma globulin.

The present inventors attacked the above-described problems of the prior art from an entirely different viewpoint to pursue a pharmaceutical preparation for intravenous administration of native gamma globulin having natural active half life and antibody activity without modifying their chemical structure. The object was to develop a preparation of the following properties:

(1) Since the gamma globulin has a native property and undergone no modification, the preparation contains none of the fragments such as Fab, F (ab')$_2$, or Fc;

(2) no decline in antibody titer nor in antibody spectrum; and (3) anticomplementary activity (complement fixing ability) is sufficiently less than a generally accepted safety limit of 20 units (C'H50 value).

In the endeavor to develop the above gamma globulin preparation, the co-worker of the present inventors invented a method for removing as a precipitate the gamma globulin aggregate, which is the cause of anticomplementary activity, by utilizing the difference in solubilities of plasma proteins in a solvent, for example, by the polyethylene glycol fractionation method (Japanese Patent Application Kokai No. 20,415/78, German Patent Application DT No. 2606118). When immediately used as such in intravenous administration, the gamma globulin preparation in liquid form obtained by the above method was found safe without side effects. Another co-worker studied the stabilizers capable of suppressing the increase in anticomplementary activity of the liquid preparation and discovered that neutral salts, glycine, saccharides, and high molecular weight nonionic active agents were significantly effective for ensuring stability of the liquid gamma globulin preparation (Japanese Patent Application Kokai No. 20,415/78). However, when a gamma globulin preparation in liquid form is stored as such, the contaminant plasminogen and the like become activated and gradually decompose the gamma globulin, resulting in a decrease in antibody titer. Moreover, a liquid protein preparation is undesirable for storage and transportation. When a liquid preparation of native gamma globulin with a low anticomplementary activity is freeze-dried by the conventional technique, the anticomplementary activity of the resulting lyophilized preparation is increased to too high a level for the safe intravenous administration. For this reason, the lyophilized native gamma globulin preparation has not yet been developed.

The present inventors conducted studies on the method for producing a lyophilized native gamma globulin preparation suitable for intravenous administration and, as a result, have accomplished the present invention based on the discovery of a suppressant which specifically controls the increase in anticomplementary activity.

The object of this invention is to provide a gamma globulin preparation in dry and stable condition, which has such properties that (1) it is in natural state without having undergone any modification nor change and contains none of the fragments of gamma globulin such as Fab, F (ab')$_2$, and Fc, (2) it is not deteriorated in antibody titer and antibody spectrum, and (3) it has an anticomplementary activity (complement fixing ability) sufficiently lower than a generally accepted safety limit of 20 units (C'H$_{50}$ value).

According to this invention, the above object is achieved by a lyophilized native gamma globulin preparation for intravenous administration comprising a human native gamma globulin having an anticomplementary activity of 20 (C'H50) or less and 0.06 to 0.26 (inclusive) part by weight of a neutral inorganic salt for 1 part by weight of the gamma globulin.

The human gamma globulin used in this invention as starting material may be prepared by any method, so long as the product has an anticomplementary activity of 20 (C'H50) or less, but a desirable material is the one which is native or in natural state and contains no Fab, F (ab')$_2$, nor Fc. It is most efficient to use an aqueous gamma globulin solution for intramuscular injection available as a drug and to break up the aggregate by acid treatment prior to use. Such a material may also be obtained from human plasma by fractionation using a nonionic surface active agent such as polyethylene glycol (F. R. German Offenlegungsschrift DT No. 2,606,118) to remove the aggregate of gamma globulin which causes development of the anticomplementary activity, thus yielding a material having an anticomplementary activity of 20 or less.

The neutral inorganic salts used to suppress the increase in anticomplementary activity are sodium chloride, potassium chloride and magnesium chloride. Of these, sodium chloride is pharmaceutically preferred. The amount used of the neutral salt is 0.06 to 0.26 (inclusive) part by weight for 1 part by weight of the gamma globulin. It is not objectionable to incorporate the preparation with, in addition to the neutral salt, 0.1 to 0.3 part by weight of human serum albumin and 0.05 to 0.15 part by weight of a nonionic surface active agent as protein stabilizers for 1 part by weight of the gamma globulin. A diluent such as mannitol may also be added in an amount of 0 to 0.5 part by weight.

The prescribed amounts of the above-noted additives are dissolved in a suitable buffer solution and mixed with an aqueous gamma globulin solution. The resulting solution is adjusted to pH 6.4 to 7.4, passed through a sterile filter and divided into portions containing each 250 to 10,000 mg of gamma globulin depending on the packaging size. Each portion of the solution is quickly freezdried in a customary way to yield a lyophilized powder preparation, the composition of which is such that the preparation contains at least 0.06 to 0.26 part by weight of a neutral salt for 1 part by weight of the gamma globulin. The product is a safe human native gamma globulin preparation for intravenous injection, which shows neither decline in antibody titer nor increase in anticomplementary activity after freeze drying, and is stable on being stored.

Prior to intravenous administration, the preparation of this invention is dissolved in water for injection to obtain a solution containing about 4 to 7% (W/V) of gamma globulin and preferably of physiologically isotonic salt concentration. The general dosage is 1,000 to 4,000 mg (containing about 50 to 60% by weight of gamma globulin) per dose for adults and 25 to 300 mg per dose for children, allowance being made within the above ranges.

Toxicity test (side effect test):

The preparation of this invention was tested for acute toxicity (mice and rats, 200 mg/kg intravenous) and subacute toxicity (rats, 50-200 mg/kg/day for 2 weeks, intravenous). None of the abnormalities indicative of toxicity was found.

Subsequent to the toxicity test, the degree of safety of the preparation of this invention was tested on 10 subjects of normal volunteers by the intravenous drip of 2,500 mg per subject under strict supervision of a physician. The test included subjective symptoms such as headache, facial flushes, diaphoresis, nausea and careful examination of blood pressure, respiratory rate, pulse frequency, body temperature and general condition before, during, and after the administration. Further, the erythrocyte sedimentation rate, hematocrit value, hemoglobin content, erythrocyte number, leucocyte number, serum protein, gamma globulin fraction, and urine were examined before and after the administration. No abnormality was found in every case, indicating sufficient safety of the preparation of this invention.

Stability test:

The results of stability test of the preparation of this invention before and after freeze drying are shown below. The sample used in the test was a fraction of gamma globlin precipitate having an anticomplementary activity of 17 units obtained by the polyethylene glycol fractionation method described in an example in F. R. German Offenlegungsschrift DT No. 2,606,118. A 0.025 molar acetate buffer solution (pH 5.1) containing 0.2 part by weight of albumin and 0.4 part by weight of mannitol, used as stabilizer and diluent, respectively, was added to 1 part by weight of the above gamma globulin fraction. To the mixture, was added 0.02 to 0.30 part by weight of sodium chloride, used as a suppressant for the increase in complementary activity. The gamma globulin was dissolved in the mixture, forming a 5% by weight solution of gamma globulin. After completion of the dissolution and adjustment of pH to 6.5, the solution was passed through a sterile filter (millipore filter). The filtrate was designated "pre-freeze-drying solution" (or simply "pre-solution" in Table 1). The powder obtained by freeze drying in a customary way was redissolved in distilled water and the solution was designated "post-freeze-drying solution" (or simply "post-solution" in Table 1). The stability was evaluated by determining the anticomplementary activity and the anti-measles antibody titer of the pre-solution and the post-solution. A sample prepared by using glycine in place of the sodium chloride and a sample prepared by adding neither sodium chloride nor glycine were used as control. If the amount of a neutral salt exceeded 0.30 part, freeze-drying became substantially impossible owing to the fusion of gamma globulin.

The assay of the anticomplementary activity was performed by the method of Kabat and Mayer [Experimental Immunochemistry, 225 (1961)]: The decrease in the number of units of a complement caused by the addition of a sample gamma globulin was determined by taking the initial number of units as 100. The anticomplementary activity was expressed in terms of the number of units which has been decreased. The anti-measles antibody titer was assayed by the Hemagglutination Inhibition Test and expressed in terms of international unit (IU/100 mg).

Table 1

| Type of additive | Amount added of glycine or NaCl | Additive (*1) Anticomplementary activity Pre-solution | Post-solution | Anti-measles antibody titer Pre-solution | Post-solution |
| --- | --- | --- | --- | --- | --- |
| Albumin only | 0 | 17 | 35 | 8 | 8 |
| Glycine | 0.45 | 16 | 32 | 9 | 9 |
| Sodium chloride | 0.02 | 16 | 23 | 10 | 10 |
| | 0.06 | 17 | 18 | 10 | 10 |
| | 0.10 | 16 | 15 | 10 | 10 |
| | 0.14 | 15 | 15 | 10 | 10 |
| | 0.18 | 15 | 15 | 10 | 10 |
| | 0.22 | 15 | 15 | 10 | 10 |

Table 1-continued

| Type of additive | Amount added of glycine or NaCl | Additive (*1) Anticomplementary activity Pre-solution | Additive (*1) Anticomplementary activity Post-solution | Anti-measles antibody titer Pre-solution | Anti-measles antibody titer Post-solution |
|---|---|---|---|---|---|
| | 0.26 | 15 | 15 | 10 | 10 |
| | 0.30 | 15 | impossible (*2) | 10 | impossible (*2) |
| Glycine | 0.45 | | | | |
| | | 15 | 17 | 9 | 9 |
| Sodium chloride | 0.06 | | | | |

Note:
(*1) Samples contain 0.2 part by weight of albumin for 1 part by weight of gamma globulin unless otherwise indicated.
(*2) "Impossible" means "freeze drying is impossible".

The above results of the stability test show the specific suppressing effect of sodium chloride on the increase in anticomplementary activity during freeze-drying. It was found that such a specific effect is exhibited by the addition of sodium chloride in an amount in the range from 0.06 part by weight per part by weight of gamma globulin to an amount sufficient for yielding a lyophilized preparation.

The gamma globulin preparation according to this invention is a lyophilized preparation having an anticomplementary activity as low as about 20 (C'H50) or less. Since the gammaglobulin, which is the major ingredient of the preparation, is in natural property without having undergone any molecular change, its physiological half-life in the blood stream is equivalent to that of the native gammaglobulin and amounts to as long as 2 to 4 weeks, far exceeding the half-life of other gamma globulin preparations for intravenous administration. The half-life of a pepsine-treated preparation is 1.25 days and that of a plasmin-treated preparation is said to be 16.5 days. Moreover, since the preparation of this invention has no newly acquired antigenic property, it is very effective for intravenous administration. The preparation of this invention may be advantageously produced by using as raw material every gamma globulin in native form which has undergone no modification.

Illustrative Examples are presented below.

EXAMPLE 1

According to the polyethylene glycol fractionation procedure described in F. R. German Offenlegungsschrift DT No. 2,606,118 (fractionation by use of polyethylene glycol in 4% (W/V), 5% (W/V), and 12% (W/V) concentrations), 15 g of gamma globulin having an anticomplementary activity of 18 were obtained from plasma protein fraction II+III. The gamma globulin was dissolved in a 0.025 molar acetate buffer solution containing finally 2.8 g of human serum albumin, 1.3 g of sodium chloride and 5.3 g of mannitol. The resulting solution was adjusted to pH about 6.7 and sterile-filtered by means of Millipore filter. The filtrate was divided into portions and each portion was freeze-dried.

The lyophilized gamma globulin had an anticomplementary activity of 18 (C'H50). The antibody titer was ×16 against epidemic parotitis, 10.1 IU/100 mg against measles, ×1024 against rubella, 144 IU/ml against vaccinia and 2.0 IU/ml against diphtheria. Since the preparation of this Example was prepared from the gamma globulin fraction obtained by the polyethylene glycol fractionation procedure, it is possibly contaminated with polyethylene glycol. Although polyethylene glycol has no special side effects as a pharmaceutical, it is preferable to remove the contaminant polyethylene glycol from the preparation.

EXAMPLE 2

A gamma globulin preparation having an anticomplementary activity of 16 (C'H50) was obtained by the fractionation procedure using polyoxyethylene-polyoxypropylene copolymer (fractionation by use of the copolymer in 6–8.5% (W/V), 8.5–10% (W/V) and 14–16% (W/V) concentrations) in place of the polyethylene glycol fractionation procedure used in Example 1. The gamma globulin preparation was treated in the same manner as in Example 1 and the results similar to those of Example 1 were obtained.

EXAMPLE 3

One hundred milliliters of a commercial 15% (W/V) aqueous solution of gamma globulin for intramuscular injection having an anti-measles antibody titer of 77 IU/100 mg and an anticomplementary activity of 69 (C'H50) were acid-treated by dialyzing against a 0.10 molar glycine buffer solution (pH 3.1) for 48 hours. The gamma globulin solution thus treated was made neutral by dialyzing against a 0.05 molar phosphate buffer solution (pH 7.0) for 24 hours. Additives were added so that the final solution may contain 0.20 part by weight of human serum albumin, 0.10 part by weight of sodium chloride and 0.40 part by weight of mannitol for 1 part by weight of gamma globulin. The resulting solution was adjusted to pH 6.5 with a 0.025 molar acetate buffer solution and sterile-filtered through Millipore filter. The filtrate was divided into portions and each portion was rapidly freeze-dried. The freeze-dried gamma globulin showed an anticomplementary activity of 12 (C'H50) and an anti-measles antibody titer of 7 IU/100 mg. These values remaind unchanged after 24 months.

EXAMPLE 4

A placental globulin obtained from a placental extract by purification was subjected to the same polyethylene glycol fractionation treatment as used in Example 1 to obtain 10 g of gamma globulin having an anticomplementary activity of 17 (C'H50). The gamma globulin was dissolved by adding a 0.025 molar acetate buffer solution containing additives so that the final solution may contain 2 g of human serum albumin and 2.5 g of sodium chloride. The resulting solution was treated in the same manner as in Example 1 and the results obtained were similar to those of Example 1.

What is claimed is:

1. A lyophilized native gamma globulin preparation for intravenous administration consisting essentially of a human native gamma globulin which has undergone no modification having an anticomplementary activity of 20 (C'H50) or less and 0.06 to 0.26 (inclusive) part by weight of sodium chloride for 1 part by weight of the gamma globulin.

2. The lyophilized native gamma globulin preparation for intravenous administration according to claim 1, wherein 0 to 0.3 part by weight of human serum albumin is incorporated for 1 part by weight of the gamma globulin.

3. The lyophilized native gamma globulin preparation for intravenous administration according to claim 1 or 2, wherein 0 to 0.5 part by weight of a diluent is incorporated for 1 part by weight of the gamma globulin.

4. The lyophilized native gamma globulin preparation for intravenous administration according to claim 3, wherein the diluent is mannitol.

5. A process for producing a lyophilized native gamma globulin preparation for intravenous administration, which comprises freeze-drying an aqueous solution of human native gamma globulin which has undergone no modification having an anticomplementary activity of 20 (C'H50) or less in the presence of 0.06 to 0.26 part by weight of sodium chloride for 1 part by weight of the gamma globulin.

6. The process according to claim 5, wherein the freeze drying is carried out in the presence of 0.1 to 0.3 part by weight of human serum albumin for 1 part by weight of the gamma globulin.

7. The process according to claim 5 or 6, wherein the freeze drying is carried out in the presence of 0 to 0.5 part by weight of a diluent for 1 part by weight of the gamma globulin.

8. A process according to claim 7, wherein the diluent is mannitol.

* * * * *